United States Patent [19]

Hillyard et al.

[11] Patent Number: 5,413,913
[45] Date of Patent: * May 9, 1995

[54] ERYTHROCYTE AGGLUTINATION ASSAY

[75] Inventors: Carmel J. Hillyard, Brisbane; Dennis B. Rylatt, Rosalie; Bruce E. Kemp, Kew; Peter G. Bundesen, Fig Tree Pocket, all of Australia

[73] Assignee: Agen Biomedical, Ltd., Acadia Ridge, Australia

[*] Notice: The portion of the term of this patent subsequent to Feb. 4, 2009 has been disclaimed.

[21] Appl. No.: 191,064

[22] Filed: Feb. 3, 1994

Related U.S. Application Data

[63] Continuation of Ser. No. 770,845, Oct. 4, 1991, abandoned, which is a continuation of Ser. No. 324,500, Mar. 16, 1989, Pat. No. 5,086,002, which is a continuation-in-part of Ser. No. 143,343, Jan. 13, 1988, Pat. No. 4,894,347, which is a continuation-in-part of Ser. No. 111,313, Oct. 22, 1987, abandoned.

[30] Foreign Application Priority Data

Sep. 7, 1987 [AU] Australia ................ PI4400
Oct. 22, 1987 [AU] Australia ................ PI5018

[51] Int. Cl.$^6$ .......................... G01N 33/555
[52] U.S. Cl. .................... 435/7.25; 435/2; 435/975; 436/519; 436/520; 436/819; 530/388.7; 530/391.1
[58] Field of Search .......... 435/2, 7.5, 70.21, 975; 436/501, 519, 520, 547, 548, 819; 530/388.1, 388.2, 388.7, 391.1

[56] References Cited

U.S. PATENT DOCUMENTS

| | | |
|---|---|---|
| 2,154,934 | 12/1936 | Hahn . |
| 3,639,558 | 2/1972 | Czismas . |
| 3,878,297 | 4/1975 | Vick . |
| 3,882,225 | 5/1975 | Patel . |
| 4,130,634 | 12/1978 | Molinaro . |
| 4,200,436 | 4/1980 | Mochida . |
| 4,292,403 | 9/1981 | Duermeyer . |
| 4,308,026 | 12/1981 | Mochida . |
| 4,331,647 | 5/1982 | Goldenberg . |
| 4,342,566 | 8/1982 | Theofilopoulos . |
| 4,358,436 | 11/1982 | Graham, Jr. . |
| 4,401,764 | 8/1983 | Smith . |

(List continued on next page.)

FOREIGN PATENT DOCUMENTS

| | | |
|---|---|---|
| 69195/81 | 10/1981 | Australia . |
| 0074271 | 3/1983 | European Pat. Off. . |
| 0096463 | 12/1983 | European Pat. Off. . |
| 0143574 | 6/1985 | European Pat. Off. . |
| 58-55759 | 4/1983 | Japan . |
| 58-203919 | 11/1983 | Japan . |
| 60-257363 | 3/1985 | Japan . |
| 60-113154 | 6/1985 | Japan . |
| 61-501418 | 7/1986 | Japan . |
| 1501819 | 6/1989 | Japan . |
| WO8504811 | 11/1985 | WIPO . |
| WO88/03650 | 5/1988 | WIPO . |

OTHER PUBLICATIONS

Bigbee, Molecul. Immunol. 20:1353–62 (1983).
Ravetch, et al., Science, 227:1593–97 (1985).
Kochan, et al., Cell, 44:689–96 (1986).

(List continued on next page.)

Primary Examiner—Esther M. Kepplinger
Assistant Examiner—Susan C. Wolski
Attorney, Agent, or Firm—Iver P. Cooper

[57] ABSTRACT

In an erythrocyte agglutination assay, the agglutination reagent comprises at least one erythrocyte binding molecule coupled to at least one specific analyte binding molecule wherein the erythrocyte binding molecule does not cause agglutination when incubated with erythrocytes in the absence of analyte (in the case of a direct assay) or analyte binding reagent (in the case of an indirect assay). Preferably, the erythrocytes are endogenous to the blood sample to be tested, that is, a whole blood sample is assayed. Mixtures of conjugates and conjugates of analyte analogues with erythrocyte binding molecules may also be used as agglutination reagents. The reagents and their use in direct or indirect assays is disclosed.

10 Claims, 4 Drawing Sheets

U.S. PATENT DOCUMENTS

| | | |
|---|---|---|
| 4,433,059 | 2/1984 | Chang et al. .......................... 436/512 |
| 4,444,753 | 4/1984 | Saikawa . |
| 4,444,878 | 4/1984 | Paulus . |
| 4,446,233 | 5/1984 | Auditore-Hargreaves . |
| 4,470,925 | 9/1984 | Auditore-Hargreaves ...... 530/387.3 |
| 4,473,495 | 9/1984 | Patterson . |
| 4,474,893 | 10/1984 | Reading . |
| 4,479,895 | 10/1984 | Auditore-Hargreaves ...... 530/387.3 |
| 4,493,793 | 1/1985 | Chu . |
| 4,517,303 | 3/1985 | Freytag . |
| 4,550,017 | 10/1985 | Liu . |
| 4,578,360 | 3/1986 | Smith . |
| 4,590,169 | 5/1986 | Cragle . |
| 4,594,327 | 6/1986 | Zuk . |
| 4,607,009 | 8/1986 | Steplewski . |
| 4,629,783 | 12/1986 | Cosand . |
| 4,661,444 | 4/1987 | Li . |
| 4,668,637 | 5/1987 | Guesdon . |
| 4,676,980 | 6/1987 | Segal . |
| 4,678,747 | 7/1987 | Lloyd . |
| 4,683,196 | 7/1987 | McLaughlin . |
| 4,695,553 | 9/1987 | Wardlaw . |
| 4,695,678 | 9/1987 | Forrest . |
| 4,735,896 | 4/1988 | Wang . |
| 4,772,547 | 9/1988 | Heimer . |
| 4,829,011 | 5/1989 | Gibbons .............................. 436/512 |
| 4,900,685 | 2/1990 | Smith, III ........................... 436/519 |
| 5,292,668 | 3/1994 | Paulus ................................ 436/547 |

OTHER PUBLICATIONS

Furthmayr, et al., BBRC 65:113–122 (1975).
Wyatt, et al., Aust. J. Med. Lab. Sci., 4:48–50 (1983).
Welling, FEBS Lett., 188:215 (1985).
Gevod and Birdi, Biophys. J., 45:1079 (1984).
DeGrado, et al., Biophys. J., 37:329.38 (1982).
Terwilliger, et al., Biophys. J., 37:353–61 (1982).
Wang, et al., PNAS (USA) 83:6159 (1986).
Rylatt, et al., Thrombosis Res. 31:767–78 (1983).
Brennan, et al., Science, 229:81–83 (1985).

KEY

REAGENT
 ANTIGEN
 ANTIBODY

NEGATIVE

+  ⇒

AGGLUTINATION

POSITIVE

+  ⇒

INHIBITION

ERYTHROCYTE AGGLUTINATION ASSAY

Cross Reference to Related Applications

This application is a continuation of application Ser. No. 07/770,845, filed Oct. 4, 1991, now abandoned which is a continuation of 07/324,500, filed Mar. 16, 1989, now U.S. Pat. No. 5,086,002, which is a continuation in part of 07/143,343, filed Jan. 13, 1988, now U.S. Pat. No. 4,894,347, which is a continuation in part of 07/111,313, filed Oct. 22, 1987, now abandoned Priority under 35 U.S.C. 119 is claimed from Australian provisional application PI 4400 filed Sep. 17, 1987. The text of all prior applications is hereby incorporated by reference into the present application.

BACKGROUND OF THE INVENTION

1. Field of the Invention

The present invention relates to a reagent and a method for detecting an antigen, antibody or other analyte in human or animal blood by erythrocyte agglutination. The invention also concerns a kit containing the reagent and processes of preparation of the reagents.

2. Information Disclosure Statement

Assaying blood samples for a particular antigen or antibody has traditionally involved the step of separating the cellular components from the serum components of the blood by centrifugation and/or clotting, prior to assay.

This presents several potential problems. Firstly, such an assay is not suited to testing being conducted under field conditions. In many veterinary situations a quick test in the field is more desirable than the alternative of transporting samples to laboratories for separation and assay. Also, veterinary surgeons who do not have access to a centrifuge frequently need to assay blood samples for the presence of infectious agents such as heartworm. Further, assays being used for the detection of diseases in Third World countries present a situation where simplicity and low cost are of the essence.

Secondly, in certain pathologic conditions, separation of the blood samples becomes difficult. Blood taken from patients suffering conditions such as Waldenstrom's macroglobulinemia is difficult to separate into serum and cell fractions making an assay which can be conducted on whole blood highly desirable.

Thirdly, blood samples are often used for testing for the presence of highly contagious and potentially dangerous disease states. In these cases it is preferable that as little handling and processing of the samples as possible is undertaken in order to minimize the risk to personnel conducting the assay. Further, certain conditions make the provision of over-the-counter finger-prick assays highly desirable. Such assays must necessarily be suited to performance on whole blood.

Immunoassays have revolutionized human diagnostic and veterinary medicine since the introduction of techniques such as the radioimmunoassay, first reported by Yalow and Berson (1959) Nature 184, 1648, and the enzyme immunoassay or EIA which was first reported by Engvall and Perlman (1971) Immunochem 8, 871 and Van Weeman and Schuurs (1971) FEBS Letters 15, 232.

Whilst such assays are based on antibody-antigen interactions the detection systems utilized are usually complex. The reagents used are generally enzyme or radiolabelled antigens, antibodies or complexes thereof which require either incubation with specific substrates and measurement of a color end-point either visually or by means of a colorimeter or measurement of radioactive decay with radiation counters to detect the presence of the analyte being tested. These assays also involve several washing steps. Most immunoassays for the detection of analytes in blood are currently of this nature. Thus, whilst these assays are sensitive, they are lengthy and involved procedures which may require expensive instrumentation, for detection of the analyte under test.

An alternative to these assays is provided by immunoassays of the type described by Gupta, et al., (1985) Journal of Immunological Methods 80:177–187. These are immunoassays in which erythrocytes and anti-erythrocyte antibodies are used in the indicator system. In these assays exogenous erythrocytes such as sheep erythrocytes are used.

In recent years it has been possible to attach antibodies to latex beads, thus providing a rapid agglutination assay. This, however, still entails the separation of the serum/plasma phase from the cellular phase and consequently requires the use of a centrifuge or filtration system. Latex agglutination assays are described in Castelan, et al., J. Clin. Pathol. (1968), 21, 638; and Singer & Plotz Am. J. Med. [1956 (Dec)], 888.

Both direct and indirect agglutination immunoassays are well known in the art. In these assays, the agglutination of particles to which antigen or antibody is bound is used to indicate the presence or absence of the corresponding antibody or antigen. A variety of particles, including particles of latex, charcoal, kaolinite, or bentonite, as well as both microbial and red blood cells, have been used as agglutinatable carriers. See Mochida, U.S. Pat. No. 4,308,026. The use of erythrocytes as indicator particles is strongly criticized by Patel, U.S. Pat. No. 3,882,225, who says that it is difficult to standardize indicator erythrocytes.

Molinaro, U.S. Pat. No. 4,130,634 describes an assay for an antigen which employs antibody-coated red blood cells. Molinaro emphasizes that the method used to couple the antibody to the erythrocyte must not destroy the reactivity of the antibody. He makes it clear that antibodies which are specific for the erythrocyte are not useful for his assay. He does mention, however, the possibility of using a hybrid antibody with one binding site specific for the antigen and the other specific for the red blood cell.

Chang, U.S. Pat. No. 4,433,059 discloses an agglutination immunoassay reagent in which two antibodies are covalently linked "tail-to-tail", i.e., so as not to alter their specificity. One antibody is specific for an antigen borne by an indicator substance, such as an erythrocyte. This antibody is preferably univalent to avoid nonspecific agglutination. The other antibody is divalent and is specific for the analyte. In preparation for the assay, fresh erythrocytes are coated with the conjugate. The double antibody conjugate-coated RBCs are then incubated with the test serum. Chang does not contemplate the assaying of whole blood samples using a nonautoagglutinating anti-RBC antibody and endogenous erythrocytes. He does not recognize that nonspecific agglutination may be avoided without resort to univalent erythrocyte binding fragments or address the use of binding substances other than antibodies. Additionally, he teaches that the analyte and RBC binding antibodies should be coupled by means of a heterobifunctional coupling agent.

Cytosignet, Inc., WO88/05913 (published 11 Aug. 1988) broadly describes an erythrocyte agglutination assay which detects an analyte in an erythrocyte-containing sample by means of a conjugate of an analyte-binding moiety and an erythrocyte-binding moiety (especially an antibody or lectin). While Cytosignet recognizes the need for constructs "which, in the absence of analyte, react only with particulates in the sample in such a manner that detectable agglutination of particulates does not occur," it is oblivious to the possibility of using an intact antibody, such as the anti-glycophorin antibody discussed later herein, as the erythrocyte binding element. Instead, it teaches use of an univalent Fab fragment of an anti-RBC antibody, which, like that of Chang, is derived from a divalent antibody which is capable of cross-linking two erythrocytes and thus of forming an agglutinate. Nor does it teach how to prepare a lectin so that "auto-agglutination" is avoided. Finally, it does not delineate any binding molecules, other than antibodies or lectins, which are useful in the proposed assay.

Smith, U.S. Pat. Nos. 4,578,360 and 4,401,764 describe a conjugate of an erythrocyte binding molecule and a label binding molecule. His label is a fluorescent, chemiluminescent, spin, enzyme or coenzyme label; an agglutination assay is not contemplated.

Smith, WO88/05913, bearing an international publication date of 11 Aug. 1988 but claiming priority from U.S. Ser. No. 8,571 of 29 Jan. 1987, describes an agglutination assay for an analyte in a whole blood sample which uses a construct comprising a RBC-binding moiety and an analyte-binding moiety, coupled by means of a bifunctional coupling agent. The exemplified RBC-binding moiety was a Fab' (i.e., univalent) fragment of a RBC-agglutinating antibody. The use of an anti-glycophrin monoclonal antibody (or a divalent binding fragment thereof) or of a mellitin fragment as the particulate-binding moiety is not taught.

Chu, U.S. Pat. No. 4,493,793 discloses the construction of a lectin-antibody or lectin-antigen covalently coupled conjugate. His Table I (incorporated by reference) sets forth the carbohydrate specificities of several lectins. He does not teach coupling such a conjugate to an erythrocyte through either the lectin or the antibody receptor.

Other "tail-to-tail" immunological conjugates are known. Segal, U.S. Pat. No. 4,676,980 sets forth the construction of a "tail-to-tail" conjugate of a target cell surface antigen-specific antibody and of a cytotoxic effector cell receptor-specific antibody. Several cross-linking methods, incorporated by reference, are described. This conjugate is intended for use in immunotherapy, in that it will cause the cellular immune system of the patient to lyse the target cell. The target cell would not, of course, be an erythrocyte endogenous to the host.

Freytag, U.S. Pat. No. 4,517,303 describes an immunolytic assay employing a conjugate of an analyte molecule and a cytolysin. The cytolysin may be (whole) mellitin. Since the Freytag assay requires that the conjugate lyse red blood cells, use of mellitin 7–26 or other nonlytic, RBC-binding peptides would be contrary to Freytag's teachings.

Li, U.S. Pat. No. 4,661,444 suggests the production of a tail-to-tail conjugate of an analyte-binding antibody and of an antibody specific for the idiotype of the first antibody. This conjugate was to be used in conjunction with an insolubilized analyte-binding antibody in an immunoassay.

Wardlaw, U.S. Pat. No. 4,695,553 teaches use of a monoclonal antibody against a universal erythrocyte antigen as a RBC agglutinating agent to clarify the interface between red blood cells and white blood cells in centrifuged whole blood. He prefers use of antibodies against glycophorin or against H antigen, but also mentions the possibility of using a mixture of lectins. Guesdon, U.S. Pat. No. 4,668,637 discusses the use of anti-red blood cell antibodies or of lectins for the purpose of erythroadsorption. Bigbee, Molecular Immunology, 20: 1353–1362 (1983) describes the production and testing of four monoclonal antibodies against glycophorin A. The general concept of using in an immunoassay an antibody which reacts with an antigenic determinant shared among all members of a class of analytes of interest (microorganisms) is set forth in McLaughlin, U.S. Pat. No. 4,683,196.

A number of patents deal with antibodies useful in blood typing. See, e.g., Lloyd, U.S. Pat. Nos. 4,678,747; Graham, Jr., 4,358,436; Liu, 4,550,017; Steplewski, 4,607,009; Lennox, WO83/03477. These antibodies are useful for blood typing because they bind to antigens found only in certain blood cell populations, while for the purpose of this invention, it is desirable to use antibodies (or mixtures thereof) which bind to essentially all erythrocytes.

Zuk, U.S. Pat. No. 4,594,327 recognizes the desirability of performing an immunoassay directly on whole blood samples. In his method, the sample is contacted with both an insolubilized, analyte-specific immunoreagent and with a red blood cell binding agent such as a RBC-specific antibody or a lectin. The analyte-specific immunoreagent and the RBC binding agent are not coupled together, and the assay disclosed is not an agglutination assay. Rather he provides assay means which filter out the red blood cells and then expose the remainder of the sample to the immunoreagent.

The problem, in an agglutination immunoassay, of nonspecific agglutination of erythrocytes by anti-erythrocyte antibodies endogenous to the blood sample, was noted by Czismas, U.S. Pat. No. 3,639,558. He proposed eliminating all naturally occurring antigenic sites on the particle by coating the particle with protein.

Theofilopoulos, U.S. Pat. Nos. 4,342,566; Duermeyer, 4,292,403 and Goldenberg, 4,331,647 are of interest as demonstrating the use of specific binding fragments of antibodies as substitutes for intact antibodies in assays. The construction of heterobifunctional antibodies is taught by Auditore-Hargreaves, U.S. Pat. Nos. 4,446,233; Paulus, 4,444,878; and Reading, 4,474,893. Mochida, 4,200,436 discloses the use of monovalent antibodies or binding fragments thereof in certain immunoassays. Forrest, U.S. Pat. No. 4,659,678 mentions that monovalent antibodies cannot form dimers or more extensive complexes with the antigen; such aggregates were said to be capable of interfering with the binding of the antigen-antibody complex to a solid phase support.

SUMMARY OF THE INVENTION

The design and use of conjugates of an erythrocyte binding antibody and an analyte binding antibody (or analyte analogue) as an agglutination reagent has been constrained by the need to avoid "auto-agglutination." By this term, we refer to the phenomenon attributable to the ability of such a reagent to bind two or more erythrocytes simultaneously, and thereby to singlehandedly cross-link the erythrocytes into an agglutinate.

The general understanding in the art is that "auto-agglutination" can be avoided only by the use of univalent erythrocyte binding molecules. Surprisingly, certain intact and therefore non-univalent antibodies, notably anti-glycophorin monoclonal antibodies, do not significantly "auto-agglutinate." It is believed that the anti-glycophorin antibody is non-autoagglutinating for steric reasons; either the binding sites of the intact antibody are able only to bind adjacent epitopes on the same erythrocyte or only one of the two binding sites can bind to glycophorin at one time. One aspect of the present invention is thus the use of intact non-auto-agglutinating anti-(RBC antigen) antibodies (or multivalent binding fragments thereof) in conjugates as described above. The use of such antibodies is advantageous because the conjugates are easier to prepare in high yields and there is no requirement to make Fab/Fab' fragments, which are difficult to purify to the necessary purity to avoid autoagglutination of cells by an agglutinating antibody.

The use of univalent derivatives of these inherently non-auto-agglutinating erythrocyte-binding antibodies is also within the scope of this invention. The advantage of using non-auto-agglutinating antibody to prepare univalent binding fragments is that it is difficult to purify Fab' from a mixture of F(ab)2 and Fab' without some F(ab)2 contamination; also, some F(ab)2 reforms from the Fab fragments. If the original antibody was itself auto-agglutinating, then any contaminating F(ab)2 will cause some agglutination. This will reduce the sensitivity of the assay. The problem is avoided, however, by deriving the Fab' fragments only from a non-auto-agglutinating antibody, as taught herein.

Another aspect of the invention is the use of a heterobifunctional hybrid antibody, one valency being for erythrocytes and the other for the analyte, as an agglutination reagent in assays for antigenic analyte. The advantages of such a hybrid antibody over a tail-to-tail conjugates, formed by a bifunctional coupling agent, of an anti-analyte antibody and a univalent fragment of anti-erythrocyte antibody are the ease of preparation, the preservation of the correct stoichiometry and stereochemistry of both antibodies and the retention of the binding affinity of each fragment.

Applicants have also discovered a new class of agglutination reagent in which the erythrocyte-binding moiety is a peptide which is not an immunoglobulin. A number of peptides are known which bind to red blood cell membranes. For example, various animal and microbial hemolytic toxins fall into this category, notably a bee venom component, mellitin. However, it is necessary to use a fragment of such peptides (or synthetic peptides corresponding to such a fragment) which do not lyse red blood cells. Also, the peptide used must not "auto-agglutinate." Thus Applicants contemplate conjugating mellitin 7-26, or other peptides with the same nonlytic, single erythrocyte-binding characteristics, with an analyte binding molecule or analyte analogue to form a direct or indirect agglutination assay reagent. The use of mellitin 7-26 instead of an anti-RBC antibody has the advantage that it can be synthesized chemically or by recombinant DNA techniques, which is more cost-effective and simpler than antibody production. However, the present invention is not limited to any particular method of preparing the EBM.

When the analyte binding molecule or analyte analogue is also a peptide or protein, the use of a peptide to bind the erythrocyte has the further advantage that the entire conjugate may be prepared without the use of a bifunctional coupling agent. Instead, a gene encoding the erythrocyte-binding peptide and the analyte binding molecule (or analogue) as a single transcriptional unit is provided, and the desired conjugate is expressed as a fusion protein, with the two moieties joined by a simple peptide bond. Alternatively, the conjugate may be prepared by direct peptide synthesis.

The present inventors further recognized that there was a need for a method which can be used in the laboratory and in the field, particularly in Third World Countries where there is lack of medical testing facilities for analysis of different types of analytes in whole blood. Under such conditions, the use of earlier methods which require separation of the blood cells from serum or plasma is difficult and in many cases impossible.

If erythrocyte-binding molecules are coupled to specific analyte-binding molecules, then the resulting conjugate could be used to bind both endogenous erythrocytes, and analytes present in a blood sample. The various novel agglutination reagents discovered by Applicants are of particular value in whole blood agglutination assays, as sensitization of heterologous red blood cells is not required or desired.

Advantages of endogenous RBC's i) Simplifies current assay procedures no need to centrifuge sample; whole blood, collected in the presence of a suitable anticoagulant, is used instead of serum or plasma.

for samples from patients with infectious diseases, such as AIDS or hepatitis, there is minimal sample handling.

appropriate for mass screening programs as conducted by the World Health Organization in third world countries, whose facilities are limited.

the assay is very robust; there is only a single reagent, which is stable in the presence of a bacteriostatic agent such as 0.01% (w/v) sodium azide.

can be used as a field test by veterinary practitioners, when the appropriate animal red cells are used for immunization to produce species specific MAb.

the test is very fast—agglutination occurs in less than three minutes.

the method can be used to monitor therapeutic drugs and patient compliance.

it also has possible use as an OTC self testing assay.

the only equipment needed is a mixing stick, glass or plastic slide, lancet and possibly a microcapillary.

ii) Advantages over exogenous erythrocytes include no pretreatment of erythrocytes. U.S. Pat. No. 4,433,059 uses blood group O negative cells, which have been spun down, reacted with antibody conjugate for 15-30 minutes and washed 3 times in PBS. U.S. Pat. No. 4,668,647 uses sheep red blood cells, which had been washed and resuspended in PBS. After the reaction, which takes place on a solid support, the cells are then fixed.

no pretreatment of samples. U.S. Pat. No. 4,433,059 notes that samples have to be heat inactivated to avoid interference due to complement. Rabbit serum and bovine albumin must also be added to minimize other non-specific reactions. None of this is necessary with the present system, where undiluted whole blood from patients may be reacted directly with reagent. This reagent contains unrelated monoclonal antibody to prevent any human anti-mouse reactions which may occur, but this not essential to the present invention.

Thus, it is possible to dispense with the cumbersome separation of cells from serum and with the sensitization and fixing of exogenous erythrocytes intended for use as indicator particles in agglutination assays. The endogenous erythrocytes are sensitized by the conjugate at the time of the assay. Applicants' invention also relates to a new method of assaying assay small antigens without repeating determinants. Conventionally, such analytes are determined by an agglutination inhibition assay. Applicants herein provide a method by which these analytes may be assayed directly. In Applicants' method, sample is incubated with both a conjugate of erythrocyte binding and analyte binding moieties, and a binding molecule specific for a new epitope formed by the binding of the first conjugate to the analyte. This allows cross-linking in the presence of the analyte to be measured. Preferably, this secondary binding molecule is also conjugated to an erythrocyte binding molecule.

DETAILED DESCRIPTION OF THE INVENTION

Figure 1:
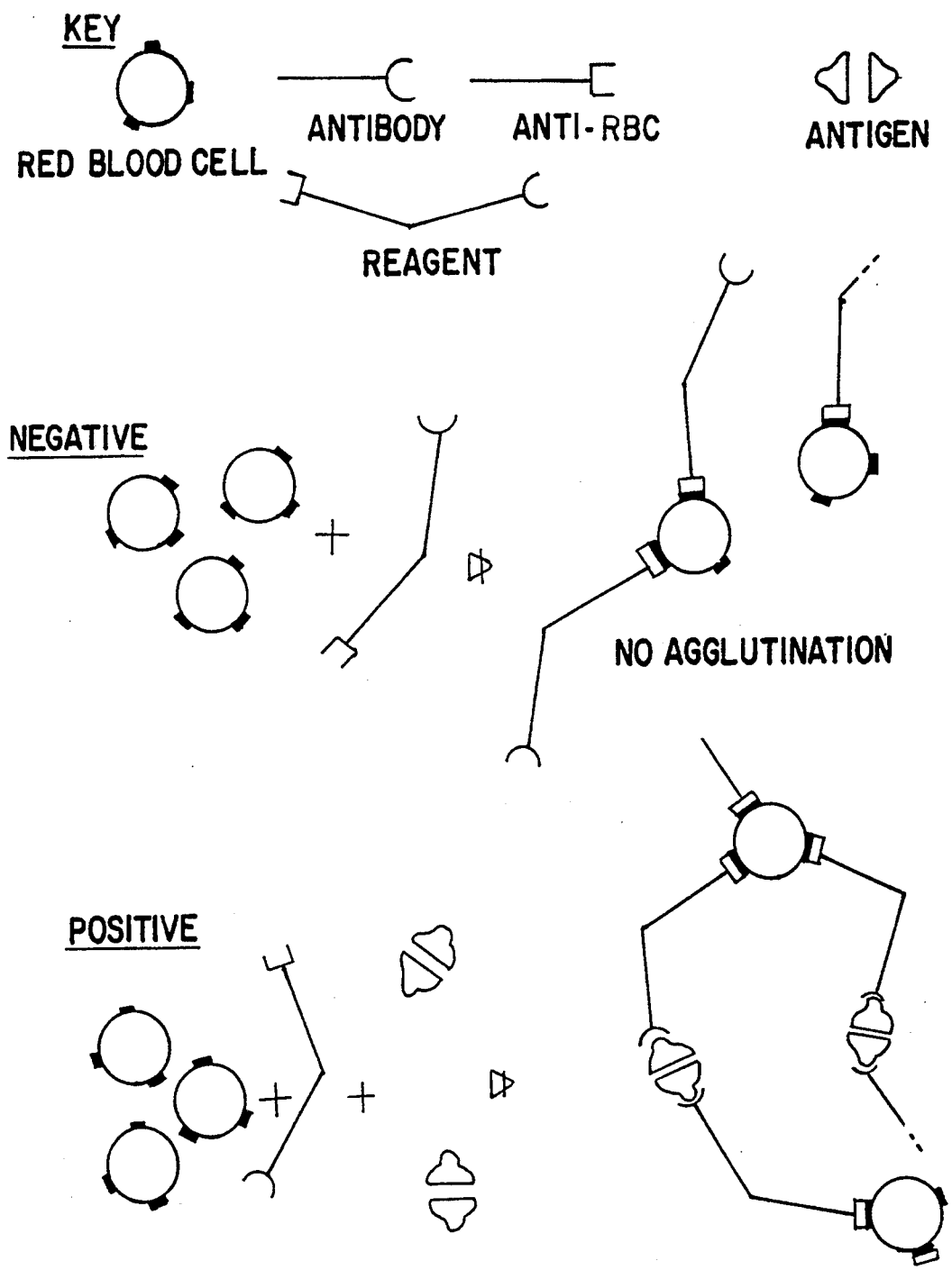
FIG. 1 is a schematic representation of erythrocytes showing positive and negative agglutination results with antibody complexes in the presence and absence of antigen respectively.
Figure 2:
FIG. 2 is a schematic representation of erythrocytes showing positive and negative agglutination results with a complex of antibody and an antigen in the presence and absence, respectively of anti-antigen antibodies.
Figure 2:
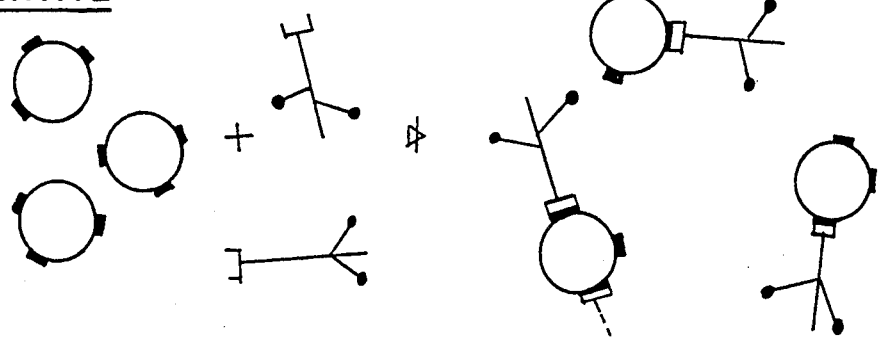
Figure 2:
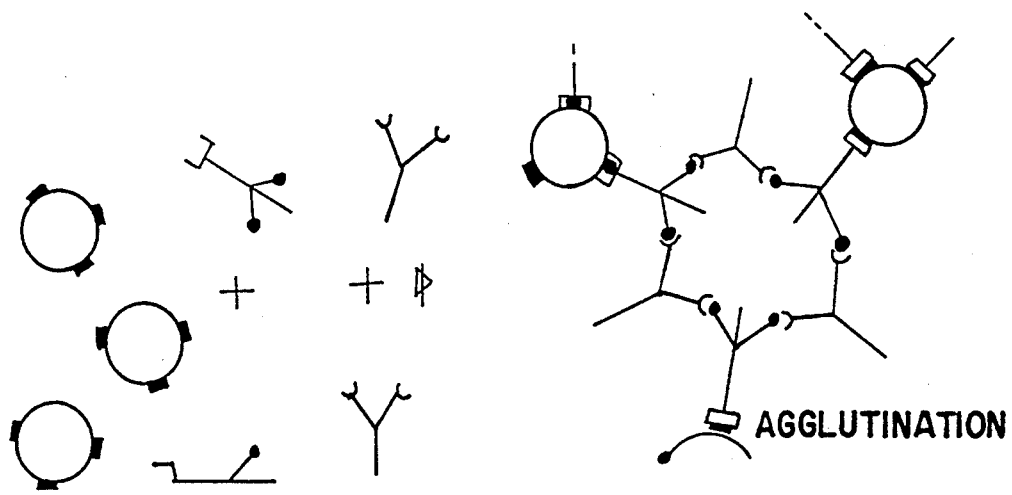
Figure 3:
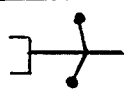
FIG. 3 is a schematic representation depicting (a) erythrocyte agglutination and (b) inhibition of erythrocyte agglutination due to presence of analyte or antigen.
Figure 3:
Figure 3:
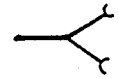
Figure 3:
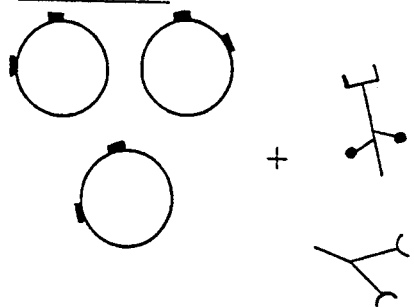
Figure 3:
Figure 3:
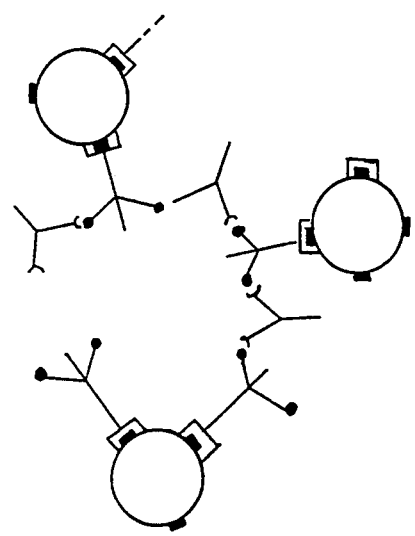
Figure 3:
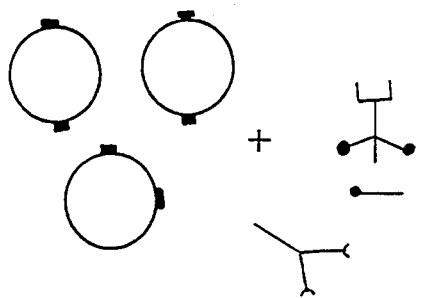
Figure 3:
Figure 3:
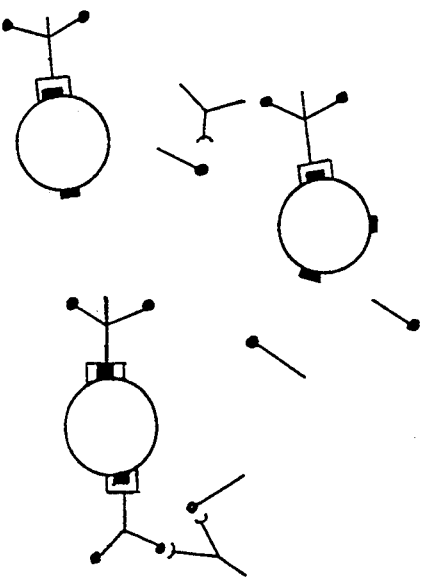
Figure 4:
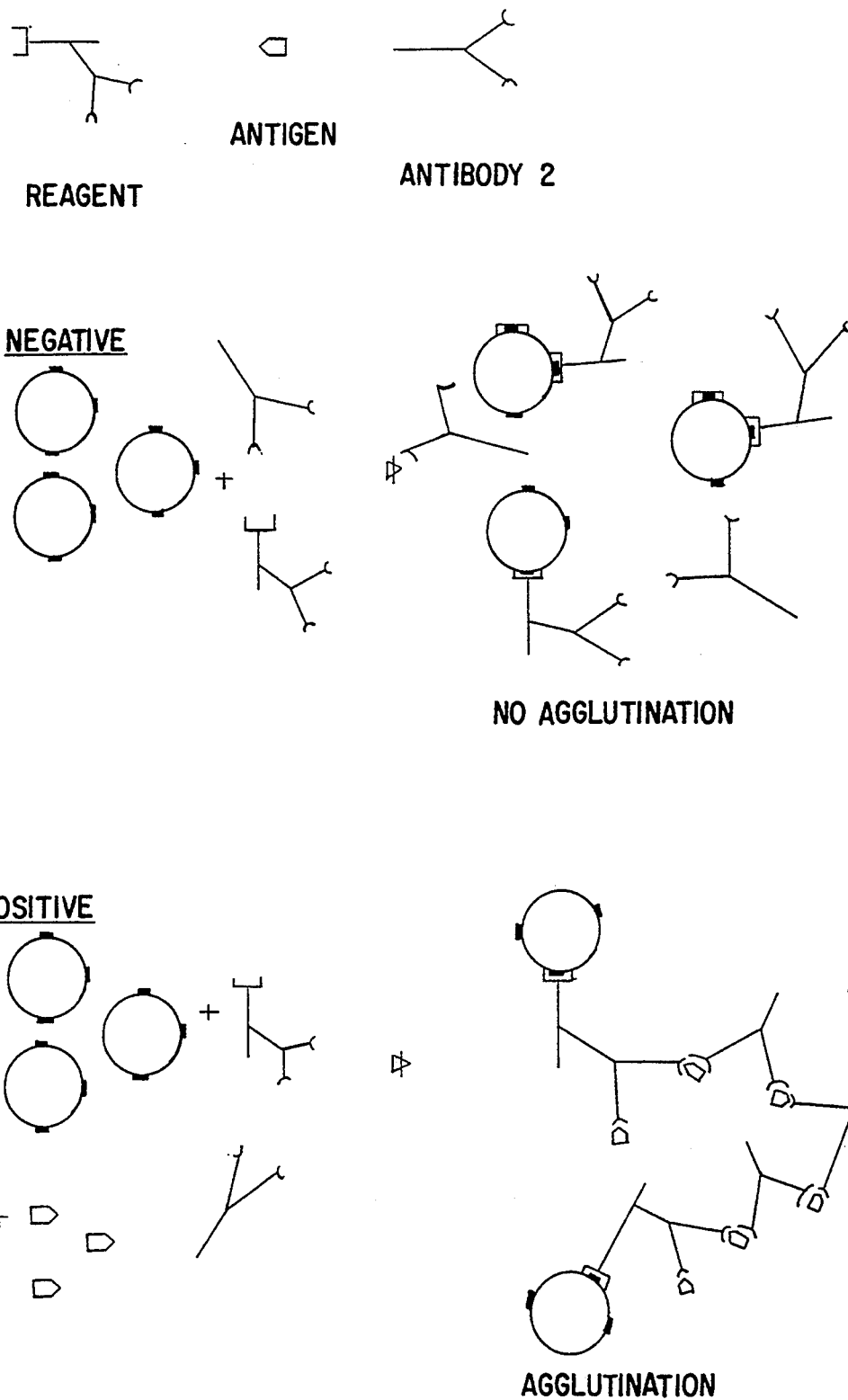
FIG. 4 is a schematic representation depicting mechanisms of agglutination/non-agglutination in connection with an overlapping antigen assay.

In the direct agglutination assay of this invention, a reagent is provided which comprises a conjugate wherein at least one erythrocyte binding molecule is coupled to at least one analyte binding molecule, without substantially changing the binding characteristics of either molecule. Alternatively, an indirect agglutination assay may be conducted using a conjugate of an erythrocyte binding molecule with an analyte analogue, and an analyte binding reagent. In either case, the erythrocyte binding molecule is one which is incapable of cross-linking erythrocytes into an agglutinate. The direct assay conjugate is thus essentially non-agglutinating when incubated with erythrocytes in the absence of the analyte, while the indirect assay conjugate is essentially non-agglutinating when incubated with erythrocytes in the absence of a multifunctional analyte binding agent.

Erythrocyte Binding Molecules

Erythrocyte membranes contain various antigenic surface constituents, including proteins, glycoproteins, glycolipids and lipoproteins. Antibodies which recognize these constituents may be prepared by conventional techniques using the membrane, or the purified constituents thereof, as immunogens. These antibodies may be monoclonal or polyclonal in nature. Either the intact antibody, or specific binding fragments thereof, may be used as erythrocyte binding molecules (EBM). The antibody or antibody fragment may be multivalent (esp. divalent) or univalent.

In addition, glycoproteins, glycolipids and other carbohydrate structures on the surface of erythrocytes are recognized by chemicals known as lectins, which have an affinity for carbohydrates. These lectins may also be used as EBMs. When a lectin is used, it is preferably a non-agglutinating lectin, or a fragment of an agglutinating lectin which includes only a single red cell binding site. Molecules with an affinity for the lipid bilayer of the membrane can also be used as EBMs. Such molecules include the membrane binding portion of mellitin and, protamine. Other very basic peptides which are capable of binding to phosphates in the lipid bilayer may be efficacious. Peptides which could be used as EBMs, with appropriate modifications to avoid lysis, include certain malaria peptides and proteins known to have affinity for the red cell membrane (Ravetch J. V., Kochan J., Perkins M. Science 1985; 227; 1593-1597. Kochan J., Perkins M., Ravetech J. V. Cell 1986; 44; 689-696). The *P. falciparum* protein GBP-130, for example, binds to glycophorin. Other receptor molecules with specific affinity for the erythrocyte surface also may be used, including other bee venom type peptides (or analogues thereof) which bind to but do not lyse red blood cells.

The preferred EBMs of the present invention will recognize erythrocyte membrane constituents found on all, or nearly all erythrocytes, so that erythrocytes endogenous to the blood sample may be used as the agglutinating particles. Such constituents include the so-called "public antigens."

Erythrocyte membranes are lipid bilayers with a variety of proteins either on the surface or with a hydrophobic portion allowing the protein to anchor in or pass through the membrane, and may have part of the molecule inside the cell. Glycophorin A is an example of a molecule which traverses the cell membrane. The blood group specificity is conferred by carbohydrate or glycolipid moieties, which are attached to membrane proteins. It is thus important that an EBM should recognize either the protein part of a membrane glycoprotein constituent, which is common to all erythrocytes of a particular species or another common structure. The ability of a bivalent EBM to agglutinate red cells will depend on steric factors, such as the mobility of the molecule and the position of the binding site above the lipid bilayer.

The components of erythrocyte membranes include: glycophorin A (MN, $En^a$, $Wr^b$), glycophorin B (Ss, 'N', U), integral membrane protein 1 (Rhesus), membrane attached glycoprotein C4 (Chido & Rodgers), integral membrane glycoprotein (anion channel), glycolipids (Lewis), glycosphingolipids (ABH, li, P, Tk), ankyrin, spectrin, protein 4-1, F-actin. [The associated blood group factors are in parentheses.] See, "The red cell membrane," S. B. Shohet & E. Beutler, in: *Hematology*, 3rd ed. Eds: Williams, Beutler, Erslev & Lichtman, 1983. (Review of all erythrocyte membrane antigens); and The red cell membrane skeleton," V. T. Marchesi. *Blood*, 61, 1-11, 1983, (Review of the skeleton proteins). Antibodies against these proteins may be of value as EBMs.

An especially preferred EBM is an antibody recognizing glycophorin. When erythrocyte sialoglycopeptides are extracted from membranes, the main fraction (approximately 75% of total) is glycophorin. This molecule comprises 131 amino acids with 16 oligosaccharide chains. Thus, this is an abundant moiety, which could allow antibody attachment without agglutinating the red cells. It is also readily available in a relatively pure form commercially, e.g., from Sigma Chemical Company. (See "Fractionation of the Major Sialoglycopeptides of the Human Red Blood Cell Membrane" H. Furthmayr, M. Tomita & V. T. Marchesi. BBRC 65, 1975, 113-122).

Another preferred EBM is mellitin 7-26. This sequence binds to the erythrocyte membrane but will not induce lysis, which requires the remainder of the sequence. Thermolysis-generated fragments of the polybasic salmon protein, protamine (PRRRRSSSRPVRRRRRPRVSRRRRRRGGRRR-R) can also be used. The whole protamine molecule causes agglutination and it is necessary to digest the molecule into fragments containing one basic sequence. These peptide EBMs are particularly advantageous when the ABM is also a peptide or protein, since then the EBM/ABM conjugate may be produced by expressing a fused gene encoding the EBM and the ABM, or by direct peptide synthesis (by, e.g., the Merrifield technique).

When the erythrocyte binding molecule is multivalent, as in the case of a normal antibody, it is desirable that the molecule recognize an erythrocyte membrane constituent which is abundant and well-distributed, and the binding site should be in such a position that cross-linking between cells is inhibited by steric hindrance, thereby avoiding premature red cell agglutination. Alternatively, cross-linking may be inhibited by the selection of an EBM that recognizes a surface constituent present in sufficient quantity so that the epitopes are sufficiently close for the binding sites on the EBM to be bound by the one RBC.

It is preferable, but not necessary, that a single EBM be used that recognizes essentially all erythrocytes. Several EBMs may be used, either in the same or in separate conjugates, each of which recognizes a particular group of erythrocytes, but which in aggregate recognize essentially all erythrocytes.

While it is preferable that the EBM recognize a natural surface constituent of the erythrocyte, it is possible to coat erythrocytes with a ligand recognized by the EBM, or to treat the erythrocytes so as to expose a normally cryptic ligand. This can be done with erythrocytes endogenous to the patient, if desired.

Analytes

This invention is not limited to the detection of any particular analyte. The analyte may be a substance normally found in blood, such as a blood protein, an antibody or a hormone, or it may be a foreign substance, such as a drug (including both therapeutic drugs and drugs of abuse), or an organism, such as a virus (by recognizing a virus coat protein) bacterium, protozoan, fungus, or multicellular parasite (e.g., heartworm).

The analyte may have repeating epitopes, recognizable by one analyte binding molecule, or unique epitopes, where a mixture of analyte binding molecules is necessary. However, analytes which can only be bound by one ABM at a time, may also be detected, as is explained later in this specification.

Analyte Binding Molecule

The analyte binding molecule may be any substance having a preferential affinity for the analyte, including monoclonal or polyclonal antibodies, lectins, enzymes, or other binding proteins or substances (or binding fragments thereof). Where the analyte is an antigen, the ABM is usually an antibody. Where the analyte is an antibody, the ABM is usually an antigen recognized by that antibody. When the analyte to be detected has no repeating epitopes, two or more ABMs are required with different specificities for the analyte. The reagent in this case will be either a mixture of EBM bound to ABM 1 and EBM bound to ABM 2, or EBM with both ABMs attached.

The analyte binding molecule need not bind the analyte directly. For example, in an assay for growth hormone, one ABM may be directed against a growth hormone binding protein if the latter is known to be present in the sample, or is separately provided.

Coupling of EBM and ABM

The EBM and the ABM may be coupled together directly or indirectly, and by covalent or non-covalent means (or a combination thereof). Covalent coupling via linking groups is preferred except (1) when the ABM and the EBM are both antibodies, in which case the conjugate is preferably a chimeric antibody as described below, or (2) when the ABM and the EBM are both peptides, in which case the conjugate is preferably produced by direct chemical synthesis or by recombinant DNA expression. Where multiple EBMs or ABMs are used, EBMs or ABMs may be coupled together, with one or more ABMs coupled directly to an EBM. The following table summarizes some of the covalent coupling methods known in the art.

Heterobifunctional

1. SPDP (N-Succinimidyl 3-2 (pyridyldithio)propionate) Neurath, et al., 1981, J. Virol., Meth., 3, 155-165.
2. MBS (m-maleimidobenzoyl-N-hydroxysuccinimide ester) Kitagaw, et al., 1976, J. Biochem., 79, 223-236.
3. SIAB (N-succinimidyl-4-iodoacetylaminobenzoate) Weltman, et al., 1983, Bio. Techniques, 1, 148-152.

Selective Bifunctional

P-isothiocyanatobenzoylchloride
U.S. Pat. No. 4,680,338.

Bifunctional

1. BSOCOES Bis[2-(succinimidooxycarbonyloxy)ethyl]sulphate Zarling, et al., 1980, J. Immunol., 124, 913-920.
2. BS Bis(sulphosuccinimidyl)suberate Staros, 1982, Biochemistry, 21, 3950-3955.
3. dimaleimide (pretreatment with S-acetylmercapto succinic anhydride and hydroxylamine) Weston, et al., Biochim. Biophys. Acta, 612: 40-49 (1980)

Other

1. Glutaraldehyde Avrameas, 1969, Immunochem., 6, 43.
2. Periodate Oxidation Nakane and Kawoi, 1974, J. Histochem. Cytochem., 22, 1084-1091.
3. Carbodiimide Of the foregoing methods of covalent coupling, conjugation with SPDP is preferred.

The EBM and the ABM may also be coupled non-covalently, for example, by (a) attaching biotin to one and avidin (or strepavidin) to the other, (b) attaching an anti-antibody to one, which then binds the other, (c) attaching protein A to one, which then binds the $F_c$ portion of the other, and (d) attaching a sugar to one and a corresponding lectin to the other.

It should be understood that in coupling the EBM and the ABM, the binding characteristics should be changed as little as possible. To avoid adverse effects on binding, if either the EBM or the ABM is an antibody its Fc portion ("tail") will be coupled to the conjugation partner. Also, it may be advantageous to provide a spacer moiety between the EBM and the ABM to reduce steric hindrance.

The EBM/ABM conjugate may be a chimeric antibody. Preparation of a chimeric antibody is the preferred method of obtaining an EBM/ABM conjugate when EBM and ABM are both antibodies. One method of constructing such a conjugate is the following:
  (a) preparing F(ab)$_2$ fragments of a selected antibody by pepsin digestion;
  (b) reducing and treating the fragments with Ellman's reagent to produce Fab fragments of the selected antibody;
  (c) thiolysing a selected specific antibody or a selected erythrocyte antibody; and
  (d) coupling the thioylated Fab fragment to the Ellman's reagent treated Fab fragment to produce a chimeric anti-erythrocyte antibody-antigen specific antibody conjugate; and
  (e) purifying the antibody product (e.g., by affinity purification) to free it from non-hybrid antibodies.

Another method is set forth below:
  (a) treating an anti-erythrocyte monoclonal antibody-producing hybridoma and an antigen specific monoclonal antibody-producing hybridoma with a distinct site-specific irreversible inhibitor of macromolecular biosynthesis;
  (b) fusing the two different monoclonal antibody-producing hybridomas with polyethylene glycol;
  (c) cloning the fused cells either in soft agarose or by limiting dilution;
  (d) selecting cloned heterohybridomas secreting chimeric anti-erythrocyte antibody-antigen specific antibody with a screening assay appropriate to the antibodies.

Preferably the inhibitor is selected from the group consisting of emetine, actinomycin D, hydroxyurea, ouabain, cycloheximide, edine and sparsomycin.

The chimeric antibody may be two half-molecules, one with specificity for erythrocytes (the EBM) and the other with specificity for the analyte (the ABM). In this case the disulfide bonds of the antibody couple the ABM to the EBM to form the conjugate. Alternatively, the two half-molecules may be specific for the same or different epitopes of the analyte. In this second case, the chimeric antibody is really two ABMs and must be coupled to an EBM to form a tripartite conjugate. Tripartite conjugates may be formed by other means, such as attaching the EBM and two ABMs to a macromolecular spacer.

The simplest agglutination reagent contemplated is one comprising a single conjugate of one EBM to one ABM. This reagent is suitable for the detection of antigens with repeating epitopes.

Antigenic analytes large enough to allow simultaneous binding of two antibody molecules, but which lack repeating epitopes, are known. They include many peptide and protein hormones. For agglutination to occur, the antigen must interact with the reagent so that at least some molecules of antigen act as a bridge between proximate erythrocytes. For assaying such analytes, it is preferable to employ a reagent comprising two or more distinct conjugates, i.e., ABM1/EBM-+ABM2/EBM where ABM1 and ABM2 bind to different, non-overlapping epitopes of the analyte. One might instead use a more complex single conjugate, ABM1/ABM2/EBM, where the spatial conformation is unlikely to favor the binding of both ABMs on the same conjugate molecule to the same analyte molecule.

Erythrocyte Agglutination Assay

Both direct and indirect agglutination assays are known in the art. In the conventional direct assay for an antigen, red cells are coated with antibody, and reacted with the sample. Multifunctional antigens act as bridges between the coated red blood cells, creating an agglutinate. In the conventional indirect assay, red cells are coated with antigen, and contacted with both a soluble antibody and with sample. Sample antigen competitively inhibits the binding of the sensitized red cells by the antibody, and hence the agglutination.

The reagent of the present invention may be used in either a direct or an indirect agglutination assay format. However, unlike conventional assays, it is not necessary to precoat erythrocytes with antibody or antigen. Rather, the reagent may be added to a blood sample containing endogenous erythrocytes, whereupon it will sensitize the cells, rendering them able to bind sample analyte (a direct assay) or to compete with sample analyte for a soluble analyte-binding molecule (an indirect assay).

For some small circulating molecules such as synthetic or natural steroids, digoxin, theophylline, etc., or drugs of abuse, i.e., phenobarbital, cannabinoids, opioids, etc., the analyte in question may be too small to provide the two necessary antigenic epitopes for antibody binding (or other "epitopes" for recognition by other binding molecules) to allow cross-linking and subsequent erythrocyte agglutination.

For the assay of small molecules, as in drug monitoring or indeed for any other antigens, an agglutination inhibition assay may be used. In this case, a two stage test is expected. The first stage would be addition of a reagent consisting of the analyte or analyte analogue coupled to the non-agglutinating EBM, and the second stage would be addition of an unconjugated ABM. (The two stages may be reversed). If analyte is present in the blood sample, the specific binding of the ABM to the EBM-analyte analogue conjugate will be inhibited, leading to a loss of agglutination. Otherwise, agglutination occurs.

When the analyte binding molecule or analyte analogue (AA) is a peptide, it is preferable that EBM also be a peptide, such as a mellitin or protamine fragment which binds without lysing red blood cells, since the conjugate may then be prepared by chemical synthesis or by expression of a fused gene, with a simple peptide bond joining the EBM and ABM (or AA) in the expression product.

The term "analyte analogue" includes both the analyte, and any substance also specifically bound by the ABM when such binding is competitively inhibited by the analyte. The analyte analogue may be anti-idiotypic antibody raised against the antigen-binding site of an analyte-binding antibody.

For the detection of such small molecules by direct agglutination assay, at least two specific monoclonal antibodies could be used. One monoclonal antibody which is capable of binding directly to the small circulating antigen would be coupled to the erythrocyte binding molecule. The second (secondary) monoclonal antibody would be incubated with the above conjugate and the analyte and would be capable of binding to a new antigenic determinant comprised of an overlapping region of the first monoclonal antibody and the antigen that exists only when the first monoclonal antibody binds antigen. Thus, the second monoclonal antibody acts as the erythrocyte "bridge," finally causes cross-linking between different red cells and allowing agglutination to occur. This method, of course, is not restricted to monoepitopic analytes. Also, other specific receptors could be used in place of monoclonal antibodies.

For stereochemical reasons, it may be difficult for a single secondary antibody molecule to bind simultaneously to two conjugate: analyte complexes. Thus, it may be preferable to conjugate the secondary antibody with an erythrocyte binding molecule.

In stating that a sample is to be incubated with a plurality of reagents it is to be understood that the contact may be simultaneous or sequential, without limitation to any particular order or duration of contact.

EXAMPLE 1

Preparation of Erythrocyte Binding Molecule (Anti-Glycophorin Antibody)

Immunization and Screening Procedure

Mice were immunized with human red blood cells and monoclonal antibodies produced by fusing the spleen cells of immunized animals with mouse myeloma cells. The antibodies were screened by both spin agglutination assay and enzyme immunoassay, where glycophorin was bound to a microtitre plate. Spin agglutination was performed by a modification of Wyatt & Street, Aust. J. Med. Lab. Sci, 4 48–50. 50 ul of cell culture supernatant was mixed with 50 ul of a 1% red blood cell suspension in a microtitre plate. The plate was mixed thoroughly and allowed to stand at room temperature (25° C.) for 15 minutes. Plates were then centrifuged at 1,000 g for 5 minutes. Before reading, all plates were inclined at an angle of approximately 45° for 5 minutes. Positive tests were characterized by a matt of agglutinated cells (strongly positive) or a distinct button of agglutination. In a negative test the cell pellet streamed. For optimal uniform readings end point titers were determined as the highest final serum dilution showing 100% agglutination and no cell streaming. For this example, antibodies which bound glycophorin, but did not agglutinate, were selected. The reaction of monoclonal antibody and glycophorin was determined by enzyme immunoassay. Microplates were coated with 10 micrograms/ml human glycophorin [Sigma Cat. No. G 7389] and washed, then incubated with serial dilutions of monoclonal antibody. After further washing, the presence of bound antibody was determined by the addition of enzyme labelled anti-mouse antibodies followed by the addition of substrate. The titre was determined to the largest dilution of monoclonal, which gave an A420 reading greater than 0.10 OD units above background.

Of 384 wells, 40 primary clones were chosen. These gave either a positive spin agglutination assay, a response to glycophorin on EIA or both.

| EIA | Spin agglutination | Number of clones |
| --- | --- | --- |
| Negative | Positive | 4 |
| Positive | Positive | 20 |
| Positive | Negative | 16 |

Subsequent absorption studies were performed to confirm that the antibodies recognized a glycophorin domain exposed on the red cell surface.

The results of the screening assays on ascitic fluid are listed below:

Ascitic Fluid Titre

| Clone | Spin Agglutination | Glycophorin EIA | Red Cell Absorption Test |
| --- | --- | --- | --- |
| RAT 1D3/167 | 512000 | <1000 | Positive |
| RAT 3D6/5 | 6400 | 1024000 | Positive |
| RAT 1C3/86 | <1000 | 1024000 | Positive |
| RAT 3B1/172 | 256000 | 2000 | Positive |
| RAT 3D3/22 | 4000 | 1024000 | Positive |
| RAT 3D5/61 | 128000 | 1024000 | Positive |
| RAT 1A2/187 | <1000 | 256000 | Positive |
| RAT 2A2/187 | <1000 | 128000 | Positive |
| RAT 1A3/129 | <1000 | 12800 | Weak |
| RAT 1C4/5 | <1000 | 128000 | Positive |
| RAT 4C3/13 | <1000 | 128000 | Positive |
| RAT 3B1/70 | <1000 | 517000 | Positive |

RAT IC3/86 has been deposited under the Budapest Treaty, with the designation G26.4.1C3/86, ATCC HB 9893. This deposit is not to be construed as a license to practice the invention claimed herein.

Purification of RAT 1C3/86

Monoclonal antibodies were purified to homogeneity from ascitic fluids by chromatography on hydroxyapatite (Stanker, et al., J. Immunol. Methods 76, 157, 1985).

EXAMPLE 2

Preparation of HIV Peptide-Ab Conjugate

The spread of the human immunodeficiency virus (HIV-1) has become a major global health problem. At present there is no recognized cure or vaccine for this disease. The diagnosis of infected individuals is a major factor in attempts to curtail the spread of the virus. Moreover, the need to prevent blood product contamination and protect health care personnel has increased the demand for simple, rapid, inexpensive and specific tests for the presence of anti-HIV antibodies.

We have made use of the patient's own red cells to provide a potential detection system for anti-HIV antibodies. This has been accomplished by selecting a non-agglutinating monoclonal antibody to human red blood cells. Chemically crosslinking this antibody with a synthetic HIV peptide antigen permitted specific agglutination of patients' red cells in the presence of antibodies to this antigen. The synthetic peptide antigen derived from gp41 of HIV-1 (residues 579–602), was chosen on the basis of the Welling procedure, FEBS LETT. 188:215 (1985) and corresponds with the region identified as a major epitope recognized by antibodies by from approximately 98% of AIDS patients. Wang, et al., Proc. Natl. Acad. Sci. USA, 83:6259 (1986).

Synthetic peptides were synthesized using the Merrifield procedure [R. S. Hodges and R. B. Merrifield, Anal, Biochem. 65, 241 (1975)] with the aid of an Applied Biosystems Model 430 synthesizer using double coupling cycles supplied by the manufacturer. The N-t-butyloxycarbonyl amino acid derivatives were obtained from the Protein Research Foundation (Osaka, Japan). Side chain protection was the same as supplied by Applied Biosystems with the exception of arginine for which the omega-$NO_2$ derivative was used. Chain assembly was monitored using ninhydrin [V. Sarin, et al., Anal. Biochem. 117, 147 (1981)]. The assembled peptides were simultaneously cleaved and deprotected using anhydrous HF containing 10% anisole (v/v) [J. M. Stewart and J. D. Young, Solid Phase Peptide Synthesis, pp 44 and 66, W. H. Freeman, San Francisco (1966)]. The crude peptide was precipitated with diethylether, washed with ethylacetate, and extracted with 60% acetonitrile in 0.1% trifluoroacetic acid (v/v). Synthetic peptides were purified by preparative reversed phase chromatography (Amicon $C_{18}$ resin, 250 A pore size 25×400 mm), eluting with a gradient of 1000 ml, 0 to 60% acetonitrile in 0.1% trifluoroacetic acid. The synthetic peptide was approximately 95% pure as judged by analytical reversed phase HPLC and by quantitative amino acid analysis following acid hydrolysis.

1. SPDP labeling of the Erythrocyte Binding Ab (RAT 1C3/86)

To 0.25 ml of 13.8 mg/ml RAT 1C3/86 was added 12.5 ul of 2 mg/ml SPDP in dimethyl formamide and the reaction was allowed to proceed for 1 hour at 25° C. Unreacted SPDP was removed by gel filtration on Sephadex G 25 and the level of SPDP labelling (1.4 moles/mole) was determined.

2. Reduction of Peptide 3.2

Peptide 3.2 (sequence RILAVERYLKDQQL-LGIWGCSGK, corresponding to residues 579–601 of the major coat protein of HIV 1) was dissolved in 1 ml of 100 mM Tris HCl, 1 mM EDTA pH 8.0 and reacted with 160 mM 2-mercaptoethanol for 45 minutes at 40° C. (Alternatively, 90 minutes at room temperature is adequate.) The reaction was terminated by the addition of 4 drops of trifluoroacetic acid (TFA) and 1 ml of aqueous 0.1% TFA. The mixture was applied to a Sep-pak (Waters) C 18 cartridge that had been treated with 20 ml of 60% acetonitrile, 0.1% TFA and equilibrated with 0.1% TFA. The reduced peptide was cycled through the Sep-pak twice before washing with 20 ml 0.1% TFA. The reduced peptide was eluted from the Sep-pak with 2×2 ml of 60% acetonitrile, 0.1% TFA. The sample was rotary evaporated to dryness prior to coupling.

3. Conjugation

The peptide was dissolved in 0.2 ml of a buffer containing 100 mM potassium phosphate, 100 mM sodium chloride and 4M guanidine HCl pH 7.4 and mixed with 2.2 mg of SPDP labelled antibody in the same buffer, but without guanidine HCl. The flask was incubated overnight at 25° C.

The degree of substitution of the antibody influenced the solubility of the conjugate; 20 moles peptide per mole of conjugate became insoluble. The range 5–7 moles of peptide per mole antibody was optimal. The capacity of the conjugate to bind red blood cells was monitored using the agglutination test with rabbit antimouse antibody and with HIV positive whole blood.

4. Gel Filtration Chromatography

Unreacted peptide and SPDP by-products were removed by gel filtration on a Superose 12 column (Pharmacia) in phosphate buffered saline and antibody containing fractions were pooled and stored at 4° C. after addition of 0.01% sodium azide as a preservative.

5. Preparation of Reagent for Assay

Two volumes of conjugates were mixed with one volume of a 10 mg/ml solution of an unrelated monoclonal antibody (Bruce 5) prepared as described in Bundesen, et al., Vet. Immun., Immunopath. 8, 245–260, 1985.

Assay Procedure

For assay, 10 ul of heparinized whole blood was placed on a glass slide. 30 ul of reagent containing 0.2 mg/ml conjugate and 2.5 mg/ml blocking monoclonal antibody was added and mixed. (A blocking monoclonal antibody was employed to prevent false positive agglutination due to antimouse antibodies.) The slide was rocked for up to three minutes and the presence or absence of agglutination noted.

Nine independent peptide/antibody conjugates were prepared and found to be active in agglutinating seropositive patients' red blood cells. Active conjugate was also prepared using m-Maleimidobenzoyl-N-hydroxysuccinimide ester as the crosslinking reagent.

Results were at least comparable in accuracy to those observed with an enzyme immunoassay using a similar antigen (Table 1).

Comparative testing of blood samples was by means of ELISA for the purpose of confirming positives and negatives obtained with the erythrocyte assay.

Control blood samples comprised ELISA negative blood samples and ELISA positive samples from infected patients. HIV positive patients were confirmed western blot positive by the Victorian State Reference Laboratory. Fairfield Hospital patients were negative either by western blot or EIA (Abbot Laboratories). Blood donors were tested by EIA (Genetic Systems). False positive or negative values are given in parentheses and were verified by EIA or western blot analysis.

TABLE 1

| Autologous Red Cell Agglutination Test. | | | |
|---|---|---|---|
| | Agglutination Test | | EIA Test |
| | +ve | −ve | +ve | −ve |
| HIV +ve patients | 42 | (1) | 43 | 0 |
| Fairfield Hospital patients | (3) | 63 | 0 | 66 |
| Healthy Blood Donors | (1) | 873 | (2) | 872 |

In order to evaluate the specificity of the test a series of synthetic peptides corresponding to other regions of the HIV-1 envelope proteins were tested for their capacity to inhibit agglutination reaction (Table 2). No unrelated peptide competed and the synthetic gp41 fragment, residues 572–591, which is missing the essential carboxyterminal epitope region, did not inhibit agglutination. The inhibition of agglutination with free synthetic antigen was useful in confirming the occasional weak positive samples. If addition of synthetic peptide had failed to inhibit agglutination this would have been indicative of a false positive related to the anti-red blood cell antibody.

Synthetic peptide (0.125 mg/ml) was added to the conjugated antibody prior to the addition of whole blood. The agglutination test was performed as described above. Common sequences are underlined.

TABLE 2

Specificity of Peptide Inhibition of Agglutination.

| | Added Synthetic Peptide (Sequence) | Inhibition of Agglutination |
| --- | --- | --- |
| | none | 0% |
| gp41 (579–601) | RILAVERYLKDQQ-LLGIWGCSGK | 100% |
| gp41 (572–591) | GIKQLARILAVER-YLKDQQ | 0% |
| gp120 (193–200) | ASTTTNYT | 0% |
| gp120 (105–117) | HEDIISLWDQSLK | 0% |
| gp120 (101–118) | VEQMHEDIISLW-DQSLKP | 0% |
| gp120 (105–129)Y$^{129}$ | HEDIISLWSQSL-KPAVKLTPLCVSY | 0% |

EXAMPLE 3

Preparation of Chimeric Antibodies (AntiGlycophorin/Anti-Human D-Dimer) and Use in Assay for D-Dimer Monoclonal antibodies RAT 1C3/86 (anti-human red blood cell) and DD-1C3/108 (anti-human D-dimer as described by Rylatt, et al., 1983, Thrombosis Res., 31, 767–778) were digested with pepsin essentially as described by Hackman, et al., 1981, Immunology, 15, 429–436, and purified by chromatography on a TSK-3000 SW column. 2 mg RAT 1C3/86 was digested for 45 minutes with 1% w/w pepsin in a buffer containing 0.1M acetic acid, 70 mM sodium chloride pH 3.5. Meanwhile, 2 mg DD-C1C3/108 was digested with 1% w/w pepsin for 2 hours in the same buffer. The reactions were terminated by the addition of 1.5M Tris to raise the pH to 8. The F(ab)2 fragments were purified by gel filtration chromatography on a TSK-3000 SW column.

Reduction of the F(ab)2, and subsequent blocking of the Fab fragment, was carried out as described by Brennan, et al., 1985, Science 229, 81–83. A 3 mg/ml F(ab)2 preparation was treated with 1 mM mercaptoethylamine, in the presence of 10 mM sodium arsenite, for 16 hours at 25° C. The Fab fragments were stabilized by reaction with 5,5'-dithiobis, (2-nitrobenzoic acid) (Ellman's reagent) for 3 hours at 25° C. The Fab fragment was then purified by gel filtration chromatography on a TSK-3000 SW column.

The thiol form of DD-1C3/108 was regenerated by reaction with 10 mM mercaptoethylamine for 30 minutes at 25° C. Excess reagent was removed by gel filtration chromatography on a TSK-3000 SW column. A mixture of the thiol DD-1C3/108 and the Ellman's reagent-treated RAT-1C3/86 was incubated for 16 hours at 25° C. as described by Brennan, et al. Finally, the chimeric antibody was purified by further gel filtration chromatography on a TSK-3000 SW column.

Preparation of Reagent

Two volumes of 0.1 mg/ml chimeric antibody was mixed with one volume of 7.5 mg/ml unrelated monoclonal antibody (Bruce 5).

Assay Procedure

For assay, 10 ul of heparinized whole blood was placed on a glass slide. 30 ul of reagent was added and mixed. The slide was rocked for three minutes and in the presence of D-dimer agglutination was observed.

EXAMPLE 4

Preparation of SPDP-Conjugated Digoxin/AntiGlycophorin Antibody Conjugate

Preparation of Digoxin/Ab Conjugate

1. Preparation of periodate oxidized digoxin
   2 ml 100 mM sodium periodate was added slowly, dropwise to 40 mg of digoxin (Sigma), suspended in 2 ml 95% ethanol and the reaction was allowed to continue for 30 minutes at 37° C. The reaction was stopped by the addition of 60 ul of 1M ethandiol. Finally, the Schiff's base intermediate was stabilized by the addition of 2 ml 40 mM cystine (30 minutes: 37° C.) and subsequent reaction with 1 ml of 15 mg/ml sodium borohydride (16 h: 25° C).

2. Reduction of cystine/digoxin conjugate
   3 ml of cystine/digoxin conjugate was reduced by the addition of 40 ul mercaptoethanol (40 minutes: 37° C.) and the product purified by chromatography on a Waters Sep-Pak C18 cartridge as described for the reduction of peptide in Example 1. After rotary evaporation, the sample was reacted with SPDP labelled RAT 1C3/86, which had been labelled with 5 propyldithiopyridine groups/antibody as described in Example 1 (16 h: 25° C.), the digoxin/antibody conjugate was purified by gel filtration chromatography on Superose 12.

EXAMPLE 5

Preparation of HIV Peptide/Anti-Glycophorin F(ab)2 Conjugate

An alternative reagent for the detection of anti-HIV antibodies uses an F(ab)2 derivative of the anti-glycophorin antibody.

RAT 1C3/86 (2 mg/ml in 70 mM acetate 100 mM sodium chloride pH 3.5) was digested with 10 ug/ml pepsin (Sigma P6887) for 40 minutes at 37° C. and the reaction terminated by the addition of 1/10 vol 1.5M Tris base. After overnight dialysis into a buffer containing 5 mM sodium phosphate pH 8.0, the antibody fragment was purified by ion-exchange chromatography on DEAE cellulose on a 5-300 mM gradient of sodium phosphate pH 8.0.

SPDP labelling of the F(ab)2 fragment, reduction of the peptide 3.2, conjugation of peptide 3.2 to F(ab)2 RAT 1C3/86, purification of the peptide conjugate, preparation of reagent for assay and testing procedure were carried out as described for the whole antibody conjugate.

F(ab)2 conjugates of other erythrocyte or analyte-binding antibodies may similarly be prepared, and may be coupled to molecules other than the HIV peptide.

EXAMPLE 6

Preparation of HIV Peptide/Anti-Glycophorin Fab' Conjugates

Other alternative reagents employ univalent Fab' fragments as the EBM.

A. Fab'-HIV peptide conjugate.

The Fab-TNB derivative of RAT 1C3/86 was prepared as described in Example 3. 2 mg of this antibody fragment in 0.1M phosphate buffer pH 7.0 was added to 1 mg of the reduced form of peptide 3.2 (prepared as described in Example 2) and allowed to react for 16 hours at room temperature. The purification and subsequent preparation of the reagent was carried out as described for the whole antibody conjugate except that for assay 0.5 mg/ml of Fab-TNB of an unrelated antibody of the same isotype was added as a blocking agent instead of an unrelated intact antibody.

Alternatively Fab'-HIV peptide conjugate could be formed from an S-carboxymethylated Fab'. F(ab)$_2$ RAT 1C3/86 prepared as described in Example 5, was reduced with 10 mM mercaptoethanol for 1 hour at room temperature in phosphate buffered saline. Then 15 mM iodoacetic acid was added and the reaction allowed to proceed for 15 minutes in the dark. Finally, the reaction was terminated by overnight dialysis into 100 vol of phosphate buffered saline. SPDP labelling of the S-carboxymethylated Fab', reduction of the peptide 3.2, conjugation of peptide to the fragment, purification and subsequent preparation of the reagent was carried out as described for the whole antibody conjugate except that for assay, 0.5 mg/ml of Fab-TNB of an unrelated antibody of the same isotype was added as a blocking agent instead of an unrelated intact antibody.

B. Fab-HIV Peptide Conjugate

Papain digestion was carried out after prior activation of papain (Sigma Cat No. P-3125) [10 mM DTT for 15 minutes at 37° C. in 100 mM sodium phosphate 2 mM EDTA pH 6.1]. One unit of activated papain was added to 3 mg of RAT 1C3/86 (2 mg/ml) in 100 mM phosphate buffer pH 6.1 and allowed to react for 1 hour at 37° C. The reaction was terminated by the addition of iodoacetamide to give a final concentration of 20 mM. After dialysis into phosphate buffered saline the antibody was purified by ion-exchange chromatography on a Waters DEAE 5PW column on a 5-500 mM gradient of sodium phosphate pH 8.0. SPDP labelling of the S-carboxymethylated Fab', reduction of the peptide 3.2, conjugation of peptide to the fragment, purification and subsequent preparation of the reagent was carried out as described for the whole antibody conjugate except that for assay, 0.5 mg/ml of Fab-TNB of an unrelated antibody of the same isotype was added as a blocking agent instead of an unrelated intact antibody.

EXAMPLE 7

Preparation of Mellitin as Alternative EBM

A peptide derived from the bee venom mellitin (CVLTTGLPALISWIKRKRQQ), was used as an alternative to the erythrocyte binding monoclonal antibody. This peptide binds to the erythrocyte surface without lysing the cell (deGrado W. F., Kezdy F. J., Kaiser E. T. J Am Chem Soc. 1981; 103; 679–81). The peptide was synthesized by the Merrifield procedure (Hodges, Merrifield. Anal. Biochem. 1975; 65; 241).

One advantage of using mellitin as the EBM is that it and a peptide-type ABM may be synthesized as a single unit, either by rDNA techniques or by Merrifield-type synthesis.

EXAMPLE 8

Use of Avidin-Biotin Linkage to Couple EBM and ABM

The ABM and EBM need not be covalently coupled. One alternative is an avidin-biotin linkage. Preparation of Biotin-Labelled Mellitin The mellitin peptide (10 mg) was reduced with mercaptoethanol as described for the 3.2 peptide in Example 1. After rotary evaporation, the sample was resuspended in 2 ml 0.1M Tris-HCl, 5 mm EDTA, pH 8.0 and reacted with 1 ml dimethylsulfoxide (DMSO), containing 4.3 mg N-iodoacetyl-N-biotinylhexylendiamine (Pierce). This was allowed to react for 15 minutes at room temperature and the biotinylated derivative separated from byproducts on a Sephadex G10 column.

Preparation of Avidin-labelled Peptide 3.2

The 3.2 peptide is coupled to avidin in the same manner as it was coupled to antibody in Example 1.

Assay

Sub-agglutinating doses of the avidin-labelled peptide are added to the red cells.

Notes

It will be understood that the avidinated and biotinylated molecules may be interchanged.

EXAMPLE 9

Assay for Heartworm in Dogs

A monoclonal antibody against canine red blood cells which does not agglutinate the cells was found by screening for non-agglutinating antibodies, using cross-linking with antimouse antibody as an indicator of binding. The antibody binds to a canine red blood cell antigen other than glycophorin. This antibody was conjugated by the method of example 3 to a specific heartworm antibody and the resulting conjugate detects heartworm in infected dogs.

We claim:

1. An agglutination reagent which comprises a conjugate comprising at least one erythrocyte binding molecule conjugated to at least one analyte specific binding molecule, wherein said conjugate
   a) does not cause significant agglutination in the absence of analyte,
   b) does not substantially alter the binding characteristics of said erythrocyte binding molecule or said analyte binding molecule, and
   c) does not lyse erythrocytes, and wherein said erythrocyte binding molecule is a univalent specific binding fragment of a non-univalent monoclonal anti-erythrocyte antibody and wherein neither said univalent fragment nor said non-univalent antibody causes significant agglutination of erythrocytes in the absence of analyte.

2. The reagent of claim 1 wherein the erythrocyte binding molecule specifically binds glycophorin.

3. A direct agglutination assay for the presence or amount of an analyte in a whole blood sample from a subject which comprises:
   (a) forming a mixture of a sample, erythrocytes, and an agglutination reagent which comprises a conjugate comprising at least one erythrocyte binding molecule conjugated to at least one analyte specific binding molecule, wherein said conjugate
      i) does not cause significant agglutination in the absence of analyte, ii) does not substantially alter the binding characteristics of said erythrocyte binding molecule or said analyte binding molecule, and iii) does not lyse erythrocytes, and wherein said erythrocyte binding molecule is a univalent specific binding fragment of a non-univalent monoclonal anti-erythrocyte antibody and wherein neither said univalent fragment nor said non-univalent antibody causes significant agglutination of erythrocytes in the absence of analyte; and (b) observing whether the erythrocytes are agglutinated; and (c) directly correlating the degree of agglutination with the presence or amount of analyte.

4. The assay of claim 3 wherein the erythrocyte binding molecule specifically binds glycophorin.

5. The method of claim 3 wherein the erythrocytes are human or canine erythrocytes.

6. An agglutination reagent which comprises a conjugate comprising at least one erythrocyte binding molecule conjugated to at least one analyte analogue, wherein said conjugate a) does not cause significant agglutination in the absence of an analyte binding reagent, b) does not substantially alter the binding characteristics of said erythrocyte binding molecule or said analyte analog, and c) does not lyse erythrocytes, and wherein said erythrocyte binding molecule is a univalent specific binding fragment of a non-univalent monoclonal anti-erythrocyte antibody and wherein neither said univalent fragment nor said non-univalent antibody causes significant agglutination of erythrocytes in the absence of analyte.

7. The reagent of claim 6 wherein the erythrocyte binding molecule specifically binds glycophorin.

8. An indirect agglutination assay for the presence or amount of an analyte in a whole blood sample from a subject which comprises:

(a) forming a mixture of a sample, erythrocytes, a soluble non-univalent analyte binding reagent which does not cause significant non-specific agglutination of erythrocytes, and an agglutination reagent which comprises a conjugate comprising at least one erythrocyte binding molecule conjugated to at least one analyte analog, wherein said conjugate i) does not cause significant agglutination in the absence of an analyte binding reagent, ii) does not substantially alter the binding characteristics of said erythrocyte binding molecule or said analyte analog, and iii) does not lyse erythrocytes, and wherein said erythrocyte binding molecule is a univalent specific binding fragment of a non-univalent monoclonal anti-erythrocyte antibody and wherein neither said univalent fragment nor said non-univalent antibody causes significant agglutination of erythrocytes in the absence of analyte; and (b) permitting said conjugate to compete with sample analyte for the analyte binding sites of the analyte binding reagent;

(c) observing whether the erythrocytes are agglutinated; and (d) inversely correlating the degree of agglutination with the presence or amount of analyte.

9. The assay of claim 8 wherein the erythrocyte binding molecule specifically binds glycophorin.

10. The method of claim 8 wherein the erythrocytes are human or canine erythrocytes.

* * * * *